United States Patent
Li et al.

(10) Patent No.: US 11,981,037 B2
(45) Date of Patent: May 14, 2024

(54) POSITIONING TOOL, ROBOTIC ARM SYSTEM AND REGISTRATION METHOD

(71) Applicant: Suzhou MicroPort Orthobot Co., Ltd., Jiangsu (CN)

(72) Inventors: Tao Li, Jiangsu (CN); Chao He, Jiangsu (CN); Zhou Jiang, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 894 days.

(21) Appl. No.: 16/850,789

(22) Filed: Apr. 16, 2020

(65) Prior Publication Data
US 2021/0197386 A1    Jul. 1, 2021

(30) Foreign Application Priority Data
Dec. 27, 2019 (CN) .......................... 201911382736.9

(51) Int. Cl.
*B25J 9/16* (2006.01)
*A61B 17/14* (2006.01)
(Continued)

(52) U.S. Cl.
CPC ............ *B25J 9/1694* (2013.01); *A61B 17/14* (2013.01); *A61B 34/20* (2016.02); *A61B 34/30* (2016.02);
(Continued)

(58) Field of Classification Search
CPC . B25J 9/1694; B25J 5/00; B25J 13/089; B25J 15/0019; B25J 15/0066; B25J 17/00;
(Continued)

(56) References Cited

U.S. PATENT DOCUMENTS

2004/0068179 A1* 4/2004 Jutras ..................... A61B 90/36
600/424
2011/0251625 A1   10/2011 Bulitta et al.
(Continued)

FOREIGN PATENT DOCUMENTS

CN    106456263 A    2/2017
CN    106999248 A    8/2017
(Continued)

*Primary Examiner* — Rachid Bendidi
(74) *Attorney, Agent, or Firm* — MUNCY, GEISSLER, OLDS & LOWE, P.C.

(57) ABSTRACT

The present disclosure provides a positioning tool, a robotic arm system, and a surgical system. The positioning tool includes a body, a registration tip, and a trackable element. The body is used to connect with a terminal of a robotic arm at one end and connect to the registration tip at the other end. The registration tip is used to abut a predetermined position. The trackable element is to be disposed on the body, the registration tip or the robotic arm and is used to communicate with a navigation device. The positioning tool provided in present disclosure is an integrated registration tool, which is able to be used to accomplish registrations for both the robotic arm and the object without replacements of the registration tool during the entire registration process, thereby simplifing the operation and shortening the operation time.

13 Claims, 4 Drawing Sheets

(51) Int. Cl.
*A61B 34/20* (2016.01)
*A61B 34/30* (2016.01)
*A61B 50/13* (2016.01)
*B25J 5/00* (2006.01)
*B25J 13/08* (2006.01)
*B25J 15/00* (2006.01)
*B25J 17/00* (2006.01)

(52) U.S. Cl.
CPC ............... *A61B 50/13* (2016.02); *B25J 5/00* (2013.01); *B25J 13/089* (2013.01); *B25J 15/0019* (2013.01); *B25J 15/0066* (2013.01); *A61B 2034/2055* (2016.02); *A61B 2034/2068* (2016.02); *B25J 17/00* (2013.01)

(58) Field of Classification Search
CPC ........ B25J 9/1689; A61B 17/14; A61B 34/20; A61B 34/30; A61B 50/13; A61B 2034/2055; A61B 2034/2068; A61B 90/11; A61B 90/39; A61B 17/15; A61B 17/17; A61B 2034/2051; A61B 2034/2059; A61B 2090/3937; A61B 17/142; A61B 17/1657; A61B 17/1732; A61B 34/70; G05B 2219/45119

See application file for complete search history.

(56) References Cited

U.S. PATENT DOCUMENTS

2017/0181806 A1* 6/2017 Itkowitz ................. A61B 34/70
2019/0167356 A1* 6/2019 Britton ................... A61B 90/50
2020/0360092 A1* 11/2020 Deng ...................... A61B 34/32

FOREIGN PATENT DOCUMENTS

| CN | 108056819 A | 5/2018 |
| CN | 109528274 A | 3/2019 |
| CN | 208989130 U | 6/2019 |
| EP | 1113760 B1 | 11/2008 |
| EP | 3295887 A1 | 3/2018 |
| WO | WO 2009/065827 A1 | 5/2009 |
| WO | WO-2016/087539 A2 | 6/2016 |
| WO | WO 2019/168863 A1 | 9/2019 |

* cited by examiner

POSITIONING TOOL, ROBOTIC ARM SYSTEM AND REGISTRATION METHOD

CROSS-REFERENCE TO RELATED APPLICATION

This application claims the priority of Chinese patent application number 201911382736.9, filed on Dec. 27, 2019, the entire contents of which are incorporated herein by reference.

TECHNICAL FIELD

The present disclosure relates to the technical field of a positioning tool, a robotic arm system, a surgical system and a registration method.

BACKGROUND

Surgical navigation systems are increasingly used in surgery, particularly the orthopedic surgery, because they can observe position of the surgical instrument in real time during surgery. For example, MAKO orthopedic surgical navigation system, Robodoc orthopedic surgical navigation system or the like use the combination of a robotic arm and a infrared optical navigation equipment, and employ the robot to assists operators in completing operations based on operators' pre-operation planning by combining the intra-operative registration technique. Among them, the registration technique is the key for connection between the robot and the navigation device. The robot obtains the position of the operation area that needs to be operated through the registration technique and performs active positioning operations or assisting surgery operations according to the surgical plan. However, the common registration tools and registration methods have the following problems:

(1). The procedure is cumbersome, which adds extra surgical time. The common registration method includes: installing a trackable element for registration on the tool at the terminal of the robotic arm; and removing the trackable element for registration on the robotic arm upon completion of the registration. The trackable element is fixedly connected to the robotic arm in most cases as the trackable element is required to be reliably mounted, which results in a time-consuming removal and installment. Moreover, when a bone registration is performed, another type of trackable element needs to be replaced for bone registration. However, the Orthopedic surgery is required to reduce exposure time of the operation area as much as possible to reduce the probability of infection while the traditional registration method increases the operating time due to the complicated procedures.

(2). The reliability and real-time performance are poor. The trackable element for registration is generally removed after completion of registration as the trackable element mounted on the terminal end of the robotic arm results in a shelter or collision during the operation. If a joint of the robotic arm malfunctions after removal of the trackable element, the position of the robotic arm terminal would become incorrect. In this case, the general approach is to use another means to calibrate the robotic arm terminal repeatedly, which would results in the poor reliability and real-time performance.

SUMMARY

The purpose of the present disclosure is to provide a positioning tool, a robotic arm system, a registration method, and a surgical system to solve problems in the prior art that the registration processes for the robotic arm and object in surgical operations are cumbersome and have poor reliabilities and real-time performances.

To solve the above technical problems, in one aspect, the present disclosure provides a positioning tool includes: a body, a registration tip, and a trackable element, the body having one end configured to connect with a terminal end of a robotic arm and the other end connected to the registration tip, the registration tip configured to abut a predetermined position, the trackable element configured to communicate with a navigation device, wherein the trackable element is disposed on the body, the registration tip or the robotic arm.

Optionally, in the positioning tool, the positioning tool includes at least three trackable elements.

Optionally, in the positioning tool, the trackable element is a reflective marker.

Optionally, in the positioning tool, the body includes a mounting structure for for installing a surgical instrument.

Optionally, in the positioning tool, the robotic arm includes a base joint and a plurality of movable joints, the plurality of movable joints including a shoulder joint, an elbow joint, a forearm joint, a wrist joint, and a rotation joint, and the trackable element is configured to be disposed on any one of the plurality of movable joints.

The disclosure also provides a robotic arm system, including a robotic arm and a positioning tool as described above.

Optionally, in the robotic arm system, the trackable element is disposed on a non-terminal joint of the robotic arm, and the corresponding joint of the robotic arm is one of the non-terminal joint on which the trackable element is disposed, a terminal joint of the robotic arm and a joint between the non-terminal joint on which the trackable element is disposed and the terminal joint.

Optionally, in the robotic arm system, the robotic arm includes a base joint and a plurality of movable joints, and the trackable element is arranged on one of the plurality of movable joints.

Optionally, in the robotic arm system, the plurality of movable joints include a shoulder joint, an elbow joint, a forearm joint, a wrist joint, and a rotation joint.

Optionally, in the robotic arm system, the positioning tool comprises at least three trackable elements.

Optionally, in the robotic arm system, the body includes a mounting feature for installing a surgical instrument.

In another aspect, the present disclosure provides a surgical system, which includes a navigation device, a control device, and a robotic arm system as described above; where, the navigation device is configured to track the trackable element in real time and collect spatial position information of the trackable element;

is the control device is configured to receive the spatial position information of the trackable element, and control movements of the robotic arm to cause the robotic arm to drive the positioning tool to move;

the control device is configured to, perform a registration of the robotic arm based on collected spatial position information of a corresponding joint of the robotic arm and spatial position information of the trackable element when the robotic arm is in a designated registration posture; and perform a registration of an object based on collected spatial position information of a corresponding joint of the robotic arm and spatial position information of the trackable element when the registration tip is in contact with a characteristic point of the object.

Optionally, in the surgical system, the surgical system includes a surgical cart, on which the control device and the robotic arm are disposed.

Optionally, in the surgical system, the surgical system comprises a navigation cart, on which the navigation device is disposed.

Optionally, in the surgical system, the surgical system is provided with a base element for providing a base coordinate system.

Optionally, in the surgical system, the trackable element is disposed on a terminal joint of the robotic arm, the body, or the registration tip, and the corresponding joint of the robotic arm is the terminal joint of the robotic arm.

Optionally, in the surgical system, the trackable element is disposed on a non-terminal joint of the robotic arm.

Optionally, in the surgical system, the robotic arm comprises a base joint and a plurality of movable joints, and the trackable element is arranged on one of the plurality of movable joints.

Optionally, in the surgical system, the plurality of movable joints include a shoulder joint, an elbow joint, a forearm joint, a wrist joint, and a rotation joint.

In still another aspect, the present disclosure provides a registration method using the positioning tool as described above, the method including:

collecting a first spatial position information of the trackable element and a first spatial position information of a corresponding joint of the robotic arm when the robotic arm is adjusted to a designated registration posture, and determining a first spatial position of the registration tip based on the collected first spatial position information to perform a registration of the robotic arm; and collecting a second spatial position information of the trackable element and a second spatial position information of the corresponding joint of the robotic arm when the registration tip is in contact with a characteristic point of the object, and determining a spatial position of the registration tip based on the collected second spatial position information to perform a registration of the object.

Optionally, in the registration method, the trackable element is disposed on a terminal joint of the robotic arm, the body, or the registration tip, and the corresponding joint of the robotic arm is the terminal joint of the robotic arm.

Optionally, in the registration method, the trackable element is disposed on a non-terminal joint of the robotic arm, and the corresponding joint of the robotic arm is one of the non-terminal joint on which the trackable element is disposed, a terminal joint of the robotic arm and a joint between the non-terminal joint on which the trackable element is disposed and the terminal joint.

In still another aspect, the present disclosure provides an electronic device including a processor and a memory. A computer program is stored on the memory, and the registration method as described above is implemented when the computer program is executed by the processor.

In still another aspect, the present disclosure provides a readable storage medium, in which a computer program is stored. When the computer program is executed by a processor, the registration method as described above is implemented.

In the positioning tool, robotic arm system, and surgical system provided in the present disclosure, the positioning tool includes a body, a registration tip, and a trackable element, the body having one end configured to connect with a terminal of a robotic arm and the other end connected to the registration tip, the registration tip configured to abut a predetermined position, the trackable element configured to communicate with a navigation device, the trackable element disposed on the body, the registration tip or the robotic arm. That is, the positioning tool provided in present disclosure is an integrated registration tool, which is able to be used to accomplish both registration for the robotic arm by collecting the spatial position information of the trackable element to register the robotic arm as the robotic arm is in a designated posture and registration for the object by collecting the spatial position information of the trackable element to register the object as the registration tip contacts a characteristic point of the object. There is no need to replace the registration tool during this process, thereby simplifing the operation and shortening the operation time. In addition, the trackable element of the positioning tool is mounted on the body, the registration tip, or the robotic arm, which would not cause obstructions or collisions during the operation. Therefore, there is no need to repeatedly install and remove the trackable element of positioning tool and it is possible for the navigation device to effectively track the spatial position of the positioning tool in real time during the whole operation, so that the visualization degree and safety of the operation are able to be improved.

BRIEF DESCRIPTION OF THE DRAWINGS

Features, properties, and advantages of implementation methods and related embodiments will be described with reference to the accompanying drawings. In the figures.

In the Figures,

11—positioning tool; 111—body; 112—registration tip; 113—trackable element; 12—robotic arm; 13—navigation device; 200—mounting flange; 300—mounting feature; 121—base joint; 122—shoulder joint; 123—elbow joint; 124—forearm joint; 125—wrist joint; 126—rotation joint; 14—surgical cart; 15—navigation cart.

DETAILED DESCRIPTION

The positioning tools, robotic arm systems, a registration method and surgical systems provided in present disclosure will be clearly described below with reference to the accompanying drawings and specific embodiments. It should be noted that, accompanying drawings are provided in a very simplified form not necessarily presented to scale, with their only intention to facilitate convenience and clarity in explaining the disclosed embodiments. Moreover, the structures shown in figures are often parts of actual structures. In particular, figures are sometimes drawn to different scales in order to give emphasis on different details.

The positioning tools, robotic arm systems, a registration method and surgical systems provided in present disclosure have no special limitations on the application environment, which can be applied to, for example, knee replacement surgeries, or other surgical operations such as joint surgeries, spine surgeries, and brain surgeries, etc. In the following description, the knee joint replacement surgery is used as an example for explanation. Correspondingly, the predetermined position and the trackable element object mentioned above is the bone in the following description, but this should not be taken as a limitation on the present disclosure.

The core idea of the present disclosure is to realize the integrated registration for both the robotic arm and the object by a single tool, so as to avoid replacement of the trackable element during the registration process to simplify operation process and shorten operation time. Besides, in registration process using such tool, there is no need to remove the trackable element, so that trackable element is able to be effectively tracked by the navigation device in real time during the whole operation, improving the visualization degree and safety of the operation.

Figure 1:
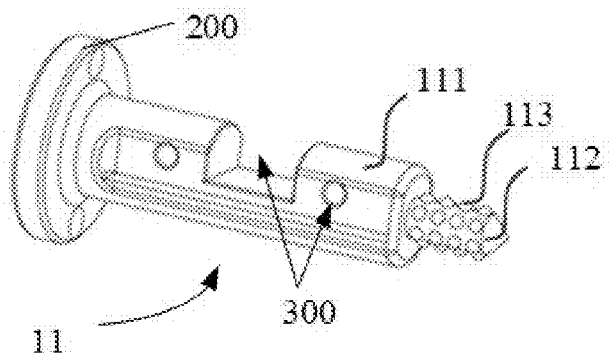
FIG. 1 is a schematic diagram of a trackable element disposed on the registration tip according to an embodiment of the present disclosure.
Figure 2:
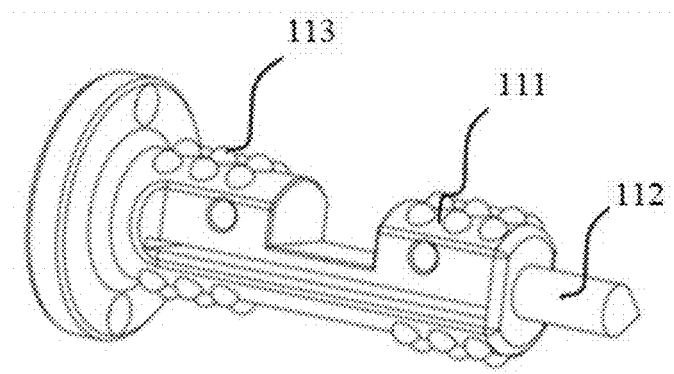
FIG. 2 is a schematic diagram of a trackable element disposed on the body according to an embodiment of the present disclosure.

Based on the above ideas, an embodiment of the present disclosure provides a positioning tool 11. Referring to FIG. 1 or FIG. 2 in combination with FIG. 5, the positioning tool 11 includes a body 111, a registration tip 112, and a trackable element 113. One end of the body 111 is configured to connect with a terminal of a robotic arm 12, and the other end of the body 111 is configured to be connected to the registration tip 112.

Figure 3:
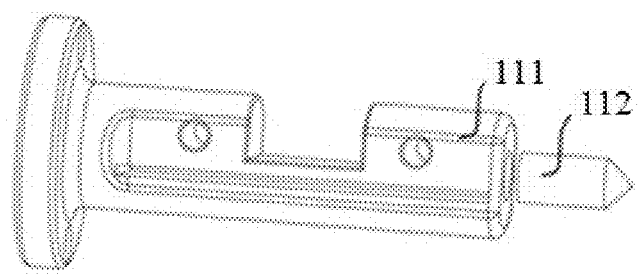
FIG. 3 is a schematic diagram of a positioning tool in a disassembled state according to an embodiment of the present disclosure.

As shown in FIG. 1, the body 111 is secured to the terminal of the robotic arm 12 through a mounting flange 200. As shown in FIG. 3, in this embodiment, it is preferable that the registration tip 112 are detachably connected to the body 111 through, for example, screw fastening connection, magnet connection or the like, to make a same registration tip 112 suitable for bodies of different types of surgery tools. But, in other embodiments, the connection between the body 11 and the registration tip 112 may be a non-detachable connection, such as an integrated connection.

The registration tip is configured to abut a predetermined position to perform a bone registration. The registration tip 112 is selected as the tapered structure as shown in FIG. 1 and FIG. 2, the tip portion of which is able to puncture the bone. Other structures having a tip portion may also be used.

The trackable element 113 is configured to be disposed on the body 111, the registration tip 112, or the robotic arm 12, so as to be tracked for spatial position information collection by a navigation device 13 in real time, where the spatial position information collected includes position information and posture information. Specifically, the spatial position information of the trackable element 113 when the robotic arm 12 is in a designated registration posture is used for registering the robotic arm 12, and the spatial position information of the trackable element 113 when the registration tip 112 is in contact with a characteristic or selected point of a bone is used to register the bone. Since the trackable element 113 does not need to be repeatedly installed and disassembled, the navigation device 13 can effectively track the spatial position of the positioning tool 11 in real time during the entire operation, thereby improving visualization degree and safety of the operation. FIG. 1 shows an example in which the trackable element 113 is provided on the registration tip 112, and FIG. 2 shows an example in which the trackable element 113 is located on the body 111.

In this embodiment, optionally, the trackable element 113 is a marking trackable element, that is, the trackable element is disposed on the positioning tool 11 or the robotic arm 12 in a marking manner. Compared with mechanically fixed trackable elements, the use of marking trackable elements saves the trouble of installation, as well as avoids loosening of the trackable elements caused by collisions during the registration process. In addition, since the trackable element 113 is used in combination with the navigation device 13, the trackable element 113 can be specifically selected according to the type of the navigation device 13. For example, when the navigation device 13 is an optical navigation device, the trackable element 113 is a reflective marker.

In this embodiment, at least three trackable elements 113 are provided, and the trackable elements 113 is distributed, for example, in a circumferential or linear manner. In other embodiments, the trackable element is not collinearly arranged to ensure that at least one trackable element 113 can be tracked.

Figure 4:
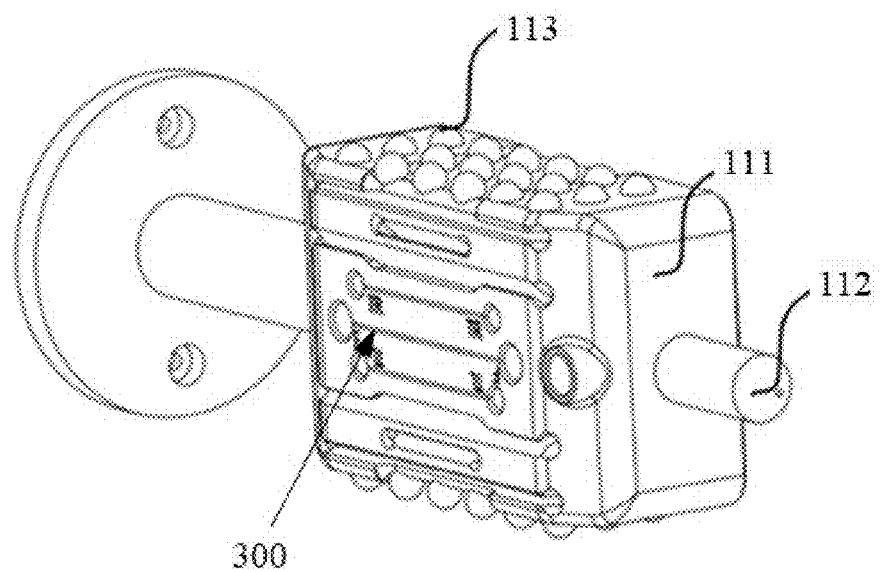
FIG. 4 is a schematic diagram of another positioning tool according to an embodiment of the present disclosure.

In this embodiment, the body 111 is selected as a structure as shown in FIG. 1. The body includes a mounting structure 300, such as an osteotomy groove and/or an osteotomy hole configured to install a surgical instrument, such as a swing saw passing therethrough. However, it should be understood that the structure shown in FIG. 1 does not intend to limit the present disclosure. In fact, in some embodiments, the tool 111 is designed as other structures configured for osteotomy guidance. FIG. 4 shows an example of another body that also includes a mounting feature 300, such as an osteotomy hole, a guiding through groove, and the like, which can be used to guide other surgical instruments, such as surgical instruments of a penetrating type.

Based on the positioning tool 11, an embodiment of the present disclosure further provides a robotic arm system. The robotic arm system includes a robotic arm 12 and a positioning tool 11.

Figure 5:
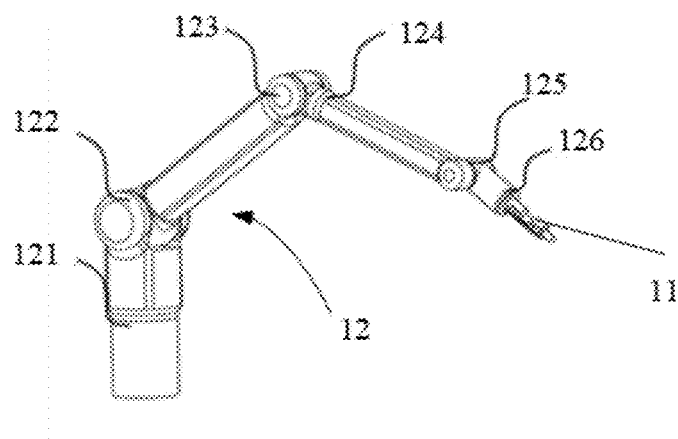
FIG. 5 is a schematic diagram of a robotic arm system according to an embodiment of the present disclosure.

Generally, a robotic arm 12 used for surgeries includes a plurality of joints. FIG. 5 illustrates an exemplary robotic arm 12 including a base joint 121, a shoulder joint 122, an elbow joint 123, a forearm joint 124, a wrist joint 125, and a rotation joint 126, where each of the shoulder joint 122, the elbow joint 123, the forearm joint 124, the wrist joint 125, and the rotation joint 126 is a movable joint. The specific spatial positions of these joints are related to the spatial position of the registration tip 112. Therefore, in the case that the spatial position of the registration tip 112 is obtained by acquiring the spatial position of the trackable element 113, if the trackable element 113 is provided on the robotic arm 12, the trackable element is preferably provided on these movable joints.

Figure 6:
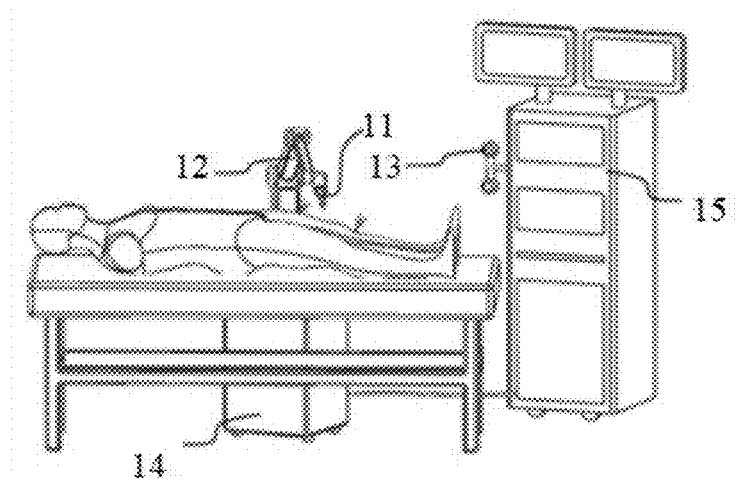
FIG. 6 is a schematic diagram of a surgical instrument system according to an embodiment of the present disclosure.

In order to further embody the core idea of present disclosure, an embodiment of the present disclosure also provides a surgical system. As shown in FIG. 6, the surgical system includes a navigation device 13, a control device (not shown), a robotic arm 12 and a positioning tool 11 as described above.

The navigation device 13 is configured to track the trackable element 113 in real time and collect spatial position information of the trackable element 113. The control device is configured to receive the spatial position information of the trackable element 113 from the navigation device 13, and control movements of the robotic arm 12 to cause the robotic arm 12 to drive the positioning tool 11 to move. The spatial position information received by the control device includes position information and posture information.

The control device is configured to: perform a registration of the robotic arm when the robotic arm 12 is in a designated registration posture through determining the spatial position of the registration tip 112 based on collected spatial position information of a corresponding joint of the robotic arm and the spatial position information of the trackable element collected by the navigation device; and perform a registration of object when the registration tip 112 is in contact with a characteristic or selected point of the object through determining the spatial position of the registration tip 112 based on collected spatial position information of a corresponding joint of the robotic arm and the spatial position information of the trackable element collected by the navigation device.

In this embodiment, the surgical system further includes a surgical cart 14 and a navigation cart 15. The navigation device 13 is provided on the navigation cart 15, and the control device is provided in the surgical cart 14 and communicates with the navigation device 13 to receive the spatial position information of the trackable element 113 collected by the navigation device 13. The base joint 121 of the robotic arm 12 is fixed on the surgical cart 14. In addition, the surgical cart 14 is provided with a power supply device for the entire surgical system. Moreover, the surgical cart 14 can also be provided with a base element that is configured to provide a base coordinate system. The base element can also be provided on the surgical cart 15 in a marking manner.

The navigation device 13 served as a visual device of the system can monitor all devices equipped with a trackable element 113. The navigation device 13 includes, but is not limited to, an optical navigation device 13, a magnetic navigation device, and an inertial navigation device 13. When the navigation device 13 is an optical navigation device, the trackable element 113 is a reflective marker.

Figure 7:
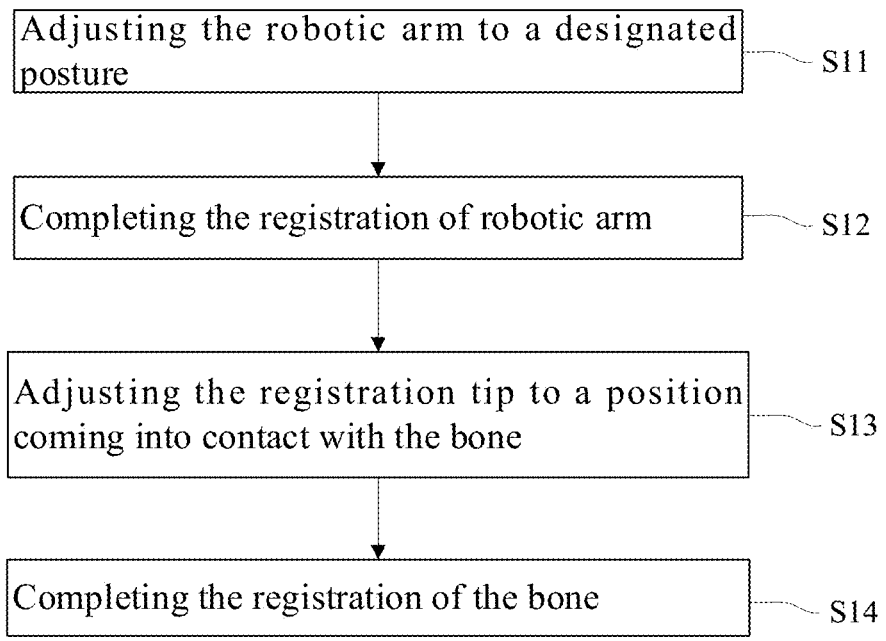
FIG. 7 is a flow chart of a registration method according to an embodiment of the present disclosure.

In addition, based on the surgical system provided in this embodiment, this embodiment also provides a registration method. As shown in FIG. 7, the registration method includes the following steps:

S11. Adjusting the robotic arm 12 to a designated registration posture;

S12. Completing the registration of the robotic arm 12, where the process includes: collecting a first spatial position information of the trackable element 113 and a first spatial position information of a corresponding joint of the robotic arm 12 when the robotic arm 12 is adjusted to a designated registration posture, and determining a first spatial position of the registration tip 112 based on the collected first spatial position information to perform a registration of the robotic arm;

S13. Adjusting the position of the registration tip to be in contact with a characteristic or selected point on a bone;

S14. Completing the registration of the bone, where the process includes: collecting a second spatial position information of the trackable element 113 and a second spatial position information of the corresponding joint of the robotic arm 12 when the registration tip 112 is in contact with a characteristic or selected point of the object, and determining a spatial position of the registration tip 112 based on the collected second spatial position information to perform a registration of the object.

When performing bone registration, an operator holds the positioning tool 11 to contact the registration tip 112 with a characteristic or selected point on the bone.

The following provides exemplary examples of the registration method provided in the embodiment of the present disclosure.

In example 1, the corresponding joint is a terminal joint of the robotic arm 12. As shown in FIG. 1, the trackable element 113 is disposed on the registration tip 112. During the registration process, the navigation device 13 collects spatial position information of the trackable element 113, and the control device acquires spatial position information of the rotation joint 126. Since the registration tip 112 and the rotation joint 126 is in a same posture, spatial position information of the registration tip 112 can be calculated by the collected spatial position information of the trackable element 113 and the collected posture information of the rotation joint 126, so that registrations of the robotic arm 12 and the bone are able to be accomplished.

In the example 2, the corresponding joint is a terminal joint of the robotic arm 12. As shown in FIG. 2 or FIG. 4, trackable element 113 is disposed on the body 111. During the registration process, the navigation device 13 collects the spatial position information of the trackable element 113, and the control device acquires the spatial position information of the rotation joint 126. Since the relative position of the trackable element 113 and the registration tip 112 is known, and the registration tip 112 and the rotation joint 126 are in a same posture, spatial position of the registration tip 112 can be calculated by the collected spatial position information of the trackable element 113 and the collected spatial position information of the rotation joint 126, so that registrations of the robotic arm 12 and the bone are able to be accomplished.

Figure 8:
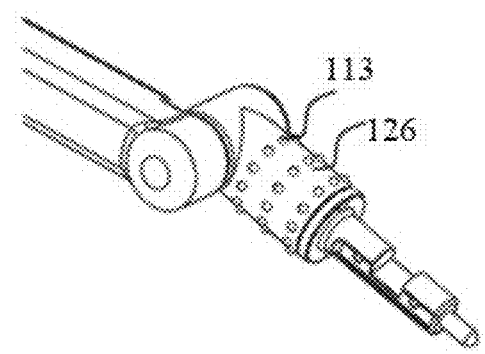
FIG. 8-FIG. 10 are schematic diagrams of a trackable element disposed on different positions of the robotic arm according to embodiments of the present disclosure.

In the example 3, the corresponding joint is a terminal joint of the robotic arm 12. As shown in FIG. 8, the trackable elements is disposed on the rotation joint 126 at the terminal of the robotic arm 12. During the registration process, the navigation device 13 collects the spatial position information of the trackable element 113, that is, the spatial position of the output axis of the wrist joint 125, and the control device acquires the spatial position information of the rotation joint 126. Since relative position between the trackable element 113 and the registration tip 112 is known, spatial position of the registration tip 112 can be calculated by the collected spatial position information of the trackable element 113 and the collected spatial position information of the rotation joint 126, so that registrations of the robotic arm 12 and the bone are able to be accomplished.

Figure 9:
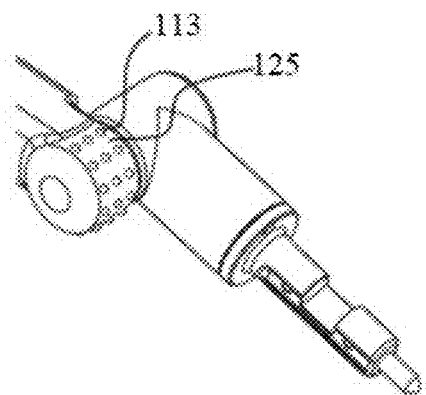

In the example 4, the corresponding joint is a non-terminal joint of the robotic arm 12. As shown in FIG. 9, the trackable element 113 is disposed on a wrist joint at the terminal of the robotic arm 12. During the registration process, the navigation device 13 collects the spatial position information of the trackable element 113, that is, the spatial position information of the output axis of the forearm joint 124, and the control device acquires the spatial position information of the wrist joint 125 and rotation joint 126. Since the relative position between the trackable element 113 and the registration tip 112 is known, spatial position of the registration tip 112 can be calculated by the collected spatial position information of the trackable element 113 and the collected spatial position information of the wrist joint 125 and rotation joint 126, so that registrations of the robotic arm 12 and the bone are able to be accomplished.

Figure 10:
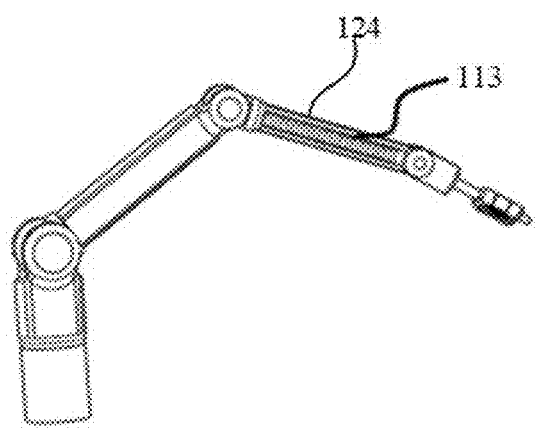

In addition, when the trackable element 113 is provided on the shoulder joint 122, elbow joint 123, and forearm joint 124, registrations of the robotic arm 12 and the bone can also be accomplished. For example, as shown in FIG. 10, in which the trackable element 113 is provided on the forearm joint 124, the corresponding joint includes the forearm joint 124, the wrist joint 125, and the rotation joint 126 and the registration process thereof is similar to the process where the trackable element 113 is disposed on the wrist joint, and thus details of the registration are not described herein again.

Further, after the registration of the robotic arm 12 and the registration of the surgical object are completed by using the registration method as described above, movements of the robotic arm 12 may be controlled based on the position information of the object to cause the robotic arm 12 to drive the positioning tool 11 to move until the registration tip 112 reaches the object. At this time, the operator holds the osteotomy saw to perform the osteotomy operation under the guidance of the positioning tool.

Based on the registration method provided in embodiments of the present disclosure, an embodiment of the present disclosure further provides an electronic device including a processor and a memory, where a computer program is stored on the memory, and the computer program is executed by the processor to implement the registration method as described above. An embodiment of the present disclosure further provides a readable storage medium, in which a computer program is stored. When the computer program is executed by a processor, the registration method as described above is implemented.

In summary, the positioning tool, robotic arm system, surgical system, and the registration method provided in the present disclosure are able to solve problems in the prior art that the registration processes for the robotic arm and object in surgical operations are cumbersome and have poor reliabilities and real-time performances.

The above description only describes the preferred embodiments of the present disclosure, and is not intended to limit the protection scope of the present disclosure. Any changes and modifications made by those skilled in the art according to the above disclosure are all within the protection scope of the appended claims.

What is claimed is:

1. A positioning tool for a robotic arm including a base joint, and a plurality of movable joints, wherein the plurality of movable joints include a shoulder joint, an elbow joint, a forearm joint, a wrist joint, and a rotation joint, wherein the positioning tool comprises: a body, a registration tip, and a trackable element that is disposed on the registration tip, the body having one end configured to connect with a terminal end of a robotic arm and the other end non-detachably connected to the registration tip, the registration tip configured to abut a characteristic point of an object to perform a registration of the object, the trackable element configured to communicate with a navigation device, wherein a mounting feature for installing a surgical instrument is provided in a middle portion of the body.

2. The positioning tool according to claim 1, wherein the positioning tool comprises at least three trackable elements.

3. The positioning tool according to claim 1, wherein the trackable element is a reflective marker.

4. A robotic arm system, comprising: a robotic arm and a positioning tool,
wherein the positioning tool comprises: a body, a registration tip, and a trackable element that is disposed on the registration tip, the body having one end configured to connect with a terminal end of the robotic arm and the other end non-detachably connected to the registration tip, the registration tip configured to abut a characteristic point of an object to perform a registration of the object, the trackable element configured to communicate with a navigation device, wherein a mounting feature for installing a surgical instrument is provided in a middle portion of the body.

5. The robotic arm system according to claim 4, wherein the robotic arm comprises a base joint and a plurality of movable joints.

6. The robotic arm system according to claim 5, wherein the plurality of movable joint comprise a shoulder joint, an elbow joint, a forearm joint, a wrist joint, and a rotation joint.

7. The robotic arm system according to claim 4, wherein the positioning tool comprises at least three trackable elements.

8. A surgical system, comprising a navigation device, a control device, and the robotic arm system according to claim 4, wherein:
the navigation device is configured to track the trackable element in real time and collect spatial position information of the trackable element;
the control device is configured to receive the spatial position information of the trackable element, and control movements of the robotic arm to cause the robotic arm to drive the positioning tool to move;
the control device is configured to: perform a registration of the robotic arm based on collected spatial position information of a corresponding joint of the robotic arm and spatial position information of the trackable element when the robotic arm is in a designated registration posture; and perform a registration of an object based on collected spatial position information of a corresponding joint of the robotic arm and spatial position information of the trackable element when the registration tip is in contact with a characteristic point of the object.

9. The surgical system according to claim 8, wherein the surgical system comprises a surgical cart, on which the control device and the robotic arm are disposed.

10. The surgical system according to claim 9, wherein the surgical cart is provided with a base element for providing a base coordinate system.

11. The surgical system according to claim 8, wherein the surgical system comprises a navigation cart, on which the navigation device is disposed.

12. The surgical system according to claim 8, wherein the robotic arm comprises a base joint and a plurality of movable joints.

13. The surgical system according to claim 12, wherein the plurality of movable joints comprise a shoulder joint, an elbow joint, a forearm joint, a wrist joint, and a rotation joint.

* * * * *